US00PP10078P

United States Patent [19]

Trees

[11] Patent Number: Plant 10,078

[45] Date of Patent: Oct. 21, 1997

[54] NEW GUINEA IMPATIENTS NAMED 'BFP-605 ORANGE'

[75] Inventor: Scott C. Trees, Arroyo Grande, Calif.

[73] Assignee: Ball Horticultural Company, West Chicago, Ill.

[21] Appl. No.: 668,131

[22] Filed: Jun. 21, 1996

[51] Int. Cl.[6] ..... A01H 5/00

[52] U.S. Cl. ..... Plt./87.6

[58] Field of Search ..... Plt./87.6

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new and distinct New Guinea impatiens cultivar named 'BFP-605 Orange' is provided. This new cultivar was the result of a controlled breeding program wherein a plant designated '307' (non-patented in the United States) was pollinated by the 'Fiji' cultivar (U.S. Plant Pat. No. 8,455). The new cultivar forms very large orange flowers that display an iridescent appearance. The foliage is medium green with reddish venation. An attractive medium upright mounded growth habit is exhibited. The new cultivar can be readily distinguished from the 'Bonfire Orange' cultivar (U.S. Plant Pat. No. 8,398).

1 Drawing Sheet

SUMMARY OF THE INVENTION

The present invention comprises a new and distinctive impatiens plant, botanically known as New Guinea impatiens, and hereinafter is referred to by the cultivar name 'BFP-605 Orange'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was a plant designated '307' (non-patented in the United States) which exhibits red blooms, dark green foliage, and a compact growth habit. The male parent (i.e., the pollen parent) was the 'Fiji' cultivar (U.S. Plant Pat. No. 8,455) which exhibits pastel pink blooms with a dark eye, and medium green foliage. The parentage of the new cultivar can be summarized as follows:

'307' × 'Fiji'.

The seeds resulting from the above pollination were sown and plantlets were obtained which were physically and biologically different from each other. Selective study resulted in the identification of a single plant of the new cultivar. This plant initially was designated BFP-605.

It was found that the new cultivar of the present invention:

(a) exhibits attractive very large orange flowers,
(b) forms medium green foliage with reddish venation,
(c) exhibits a good basal branching character, and
(d) exhibits a medium upright growth habit.

Asexual reproduction of the new cultivar by terminal or stem cuttings taken during 1993, at Arroyo Grande, Calif., U.S.A. has demonstrated that the characteristics of the new cultivar as herein described are firmly fixed and are retained through successive generations of such asexual propagation.

The 'BFP-605 Orange' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Bonfire Orange' cultivar (U.S. Plant Pat. No. 8,398), it is found that the new cultivar exhibits larger flowers and darker foliage.

Plants of the new cultivar are marketed under the CELEBRATION trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Medium upright, and mounded. A mature plant commonly measures approximately 7.5 to 9 cm. in height and approximately 20 to 28 cm. in width. This compares to a height of approximately 9 to 13 cm. and width of approximately 25 to 30 cm. for the 'Bonfire Orange' cultivar.

*Foliage.*—The configuration is elliptic with an acuminate apex and an acuminate base. The mature leaves of the new cultivar measure approximately 8.6 to 11 cm. in length × approximately 3.5 to 4 cm. in maximal width compared to approximately 9.2 to 9.5 cm. in length × approximately 2.5 to 3.5 cm. in maximal width for the 'Bonfire Orange' cultivar. The leaf margins are serrate (as illustrated). The mature foliage of new cultivar is medium green, Green Group 139A with veins of Greyed-Purple Group 185C (adaxial), and Green Group 139B with veins of Greyed-Purple Group 185A (abaxial). This compares to Yellow-Green Group 147A (adaxial) and Yellow-Green Group 147C (abaxial) for the 'Bonfire Orange' cultivar. The stem coloration is Greyed-Purple Group 183D. This compares to Greyed-Purple Group 184A for the 'Bonfire Orange' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—Orange-Red Group 33A (adaxial), and Orange-Red Group 32B with a midvein of Red Group 53D (abaxial). This compares to Orange-Red Group 33A (adaxial) and Orange-Red Group 32B (abaxial) for the 'Bonfire Orange' cultivar.

*Quantity of flowers.*—Approximately 3 to 5 per axil compared to approximately 4 to 6 per axil for the 'Bonfire Orange' cultivar.

*Number of petals.*—Five, and overlapping.

*Petal shape.*—Heart-shaped, with the superior petal generally having a broader base than the others.

*Flower size.*—Approximately 7 to 7.4 cm. in length and approximately 6.6 to 7 cm. in width. This can be compared to approximately 4.7 to 5 cm. in length and approximately 4.7 to 5 cm. in width for the 'Bonfire Orange' cultivar.

*Flower buds.*—Ellipsoidal in configuration, and generally covered with three sepals plus two rudimentary sepals fused into the under surface of the superior petal. A spur originating from the base of the inferior sepal is approximately 6.5 to 7.2 cm. in length on fully opened flowers which can be compared to approximately 4.5 to 4.7 cm. for the spur of the 'Bonfire Orange' cultivar. The spur coloration is Greyed-Purple Group 185A which can be compared to Red Group 47B for the 'Bonfire Orange' cultivar.

*Reproductive organs.*—The stamens are Red Group 43C at the base and fade to Whim Group 155D at the outer edge. The anthers tend to be fused together forming one organ that surrounds the pistil. Commonly the anthers shed pollen prior to the stigma becoming receptive. The pollen coloration is Yellow-Orange Group 16C and the ovary coloration is Green Group 143A. This can be compared to a stamen coloration of Red-Purple Group 63B, a pollen coloration of White Group 155D, and an ovary coloration of Yellow-Green Group 144B for the parent 'Bonfire Orange' cultivar.

I claim:

1. A new and distinct cultivar of New Guinea impatiens plant named 'BFP-605 Orange', substantially as herein shown and described, which:

(a) exhibits attractive very large orange flowers,
(b) forms medium green foliage with reddish venation,
(c) exhibits a good basal branching character, and
(d) exhibits a medium upright growth habit.

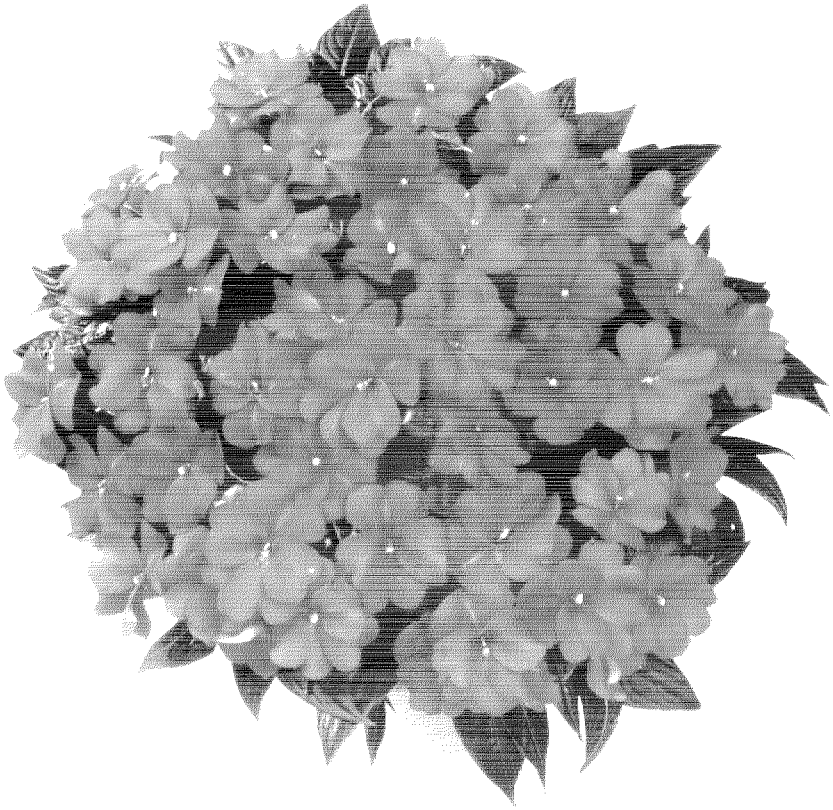

* * * * *